United States Patent [19]

McKinley

[11] 4,418,564

[45] Dec. 6, 1983

[54] SNAP ACTION BOTTLE FINISH TESTER AND METHOD

[75] Inventor: John A. McKinley, Clarion, Pa.

[73] Assignee: Owens-Illinois, Inc., Toledo, Ohio

[21] Appl. No.: 332,410

[22] Filed: Dec. 21, 1981

[51] Int. Cl.³ .............................................. G01N 3/34
[52] U.S. Cl. ....................................................... 73/12
[58] Field of Search .................... 73/12; 209/522, 523, 209/538, 599

[56] References Cited

U.S. PATENT DOCUMENTS

| | | | |
|---|---|---|---|
| 2,281,324 | 4/1942 | Preston | 73/12 |
| 2,377,536 | 6/1945 | Wisner | 73/12 X |
| 2,978,635 | 4/1961 | Oakes | 73/12 X |
| 3,067,605 | 12/1962 | Bliss | 73/12 |

*Primary Examiner*—Charles A. Ruehl
*Attorney, Agent, or Firm*—Gerald T. Welch; Myron E. Click

[57] ABSTRACT

An apparatus for testing the necks of glass containers by physically impacting the neck of each container, on the side, at 90° intervals therearound. Two embodiments are disclosed. In one, the containers are moved, in series, past four neck impacting devices and rotated between impacts. In the other embodiment, the containers move, in series, past four impacters that are so oriented and driven as to impact a non-rotatable container at 90° intervals about the neck circumference.

11 Claims, 8 Drawing Figures

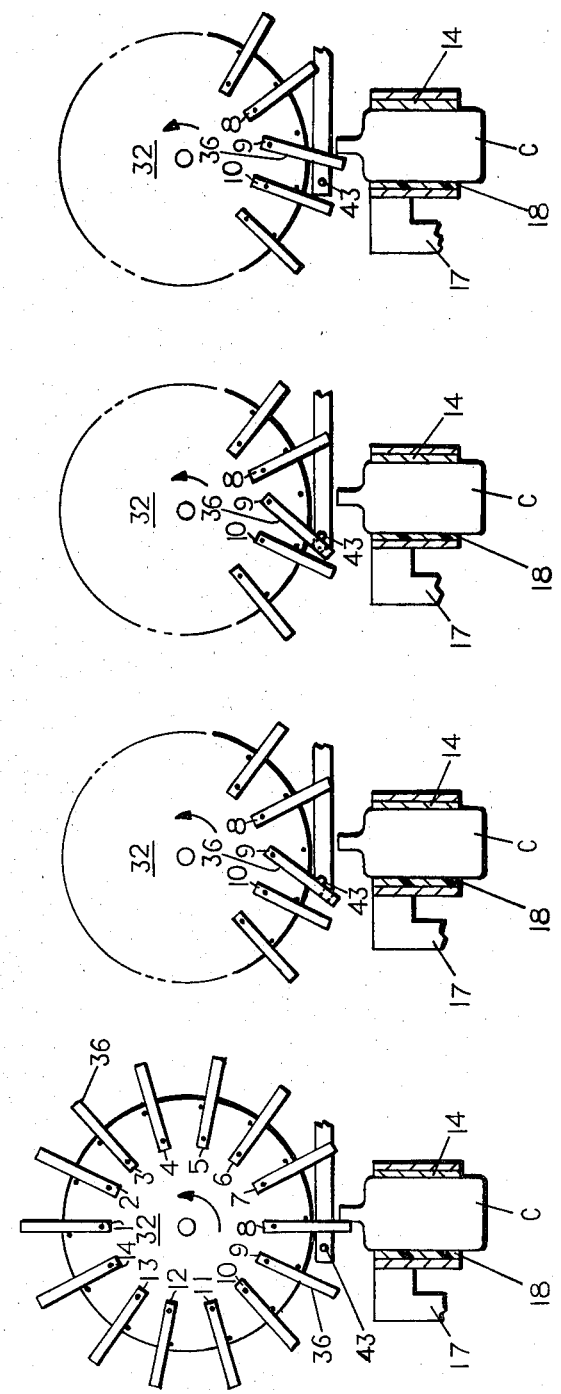

SNAP ACTION BOTTLE FINISH TESTER AND METHOD

BACKGROUND OF THE INVENTION

In the production of glass containers, particularly those which are of relatively short height and have threaded necks, for example, those glass containers used to package nail polish, they have sometimes been produced with minute cracks at the base of the neck or finish. These small cracks, or checks, as they are termed, may lead to a failure of the neck of the container when the container is filled with product and the threaded closure applied. Failure may also occur in containers with these small checks formed therein, when the closure is being removed by the consumer, or when re-applying the closure after having used a portion of the product.

There have been standard impact testing equipment for selecting glass containers; however, these have been of a type where a pendulum is used to swing an indentor into a container and typically these tests involve taking a sample container and impacting the container at increasing pendulum heights until such time as the container will fail. Further tests have been made on containers, again using the pendulum, where a percentage of the containers are impacted to a given degree as a representative sample of the containers and it is determined from this what the percentage of failure of the entire production run might be.

With this in mind, it is an object of this invention to provide an apparatus which may be located in the glass manufacturing plant and which will separate those containers which have defective or checked finishes, from those which are of acceptable strength. It is also an object of this invention to provide a method of testing the strength of the necks of glass containers by impacting the necks of the containers from the side at a plurality of points about the circumference of the neck of the container; such impacting resulting in failure of the necks which are defective; and the passing of those which are acceptable.

The present invention has as a further objective the testing of all bottle finishes of a production run immediately after they have been completely formed and have passed out of the annealing lehr.

SUMMARY OF THE INVENTION

Method and apparatus for testing glass containers to determine and segregate those with weak finishes, or necks, from acceptable ones by moving the containers through a test zone where each container is impacted with a preselected force at the side of the neck at 90° intervals about the circumference thereof, with the result that containers with weak necks are fractured and removed from the line.

BRIEF DESCRIPTION OF THE DRAWINGS

FIGS. 2, 3, 4 and 5 are schematic end views illustrating the sequence of operation of the apparatus;

DETAILED DESCRIPTION OF THE DRAWINGS

Figure 1:
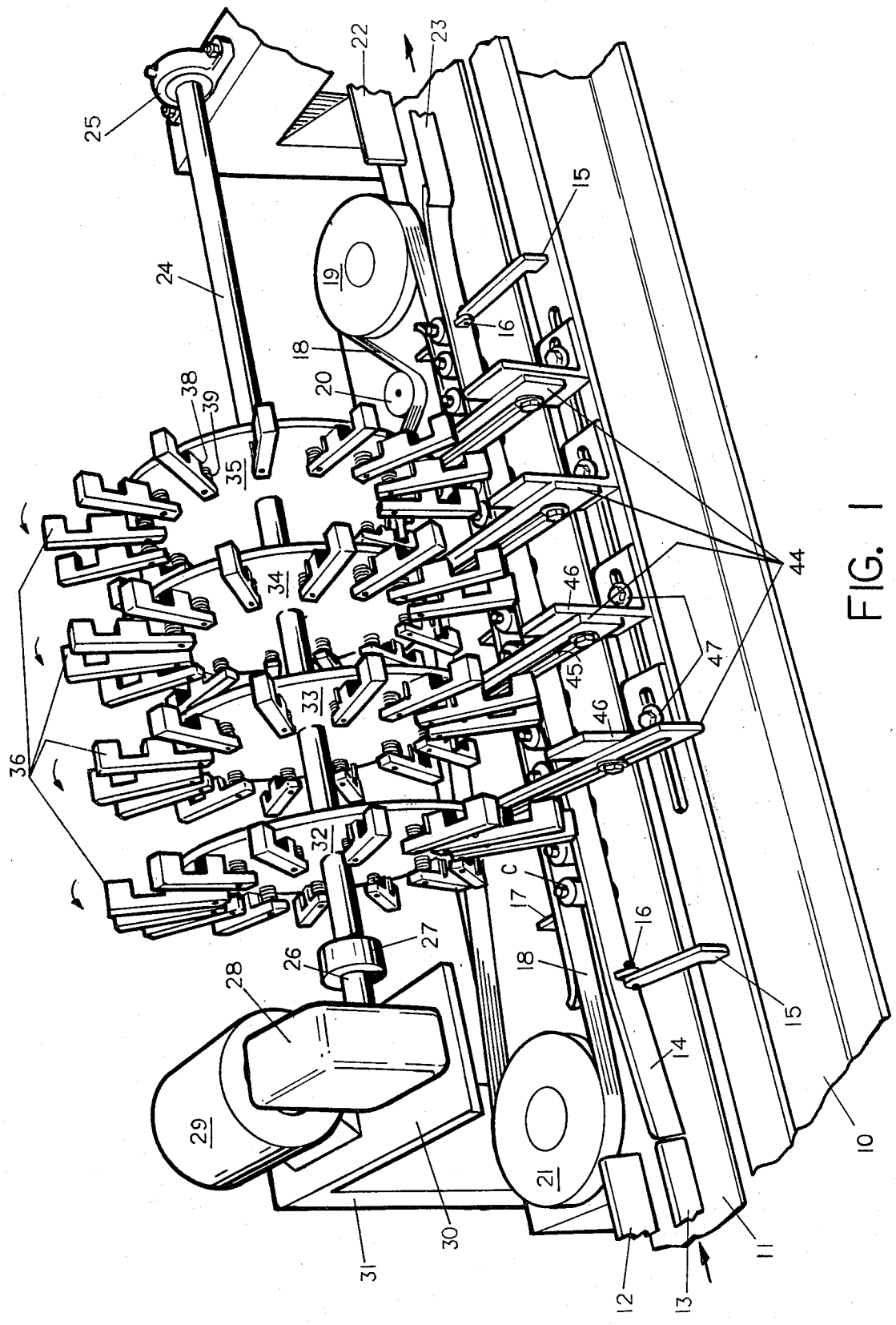
FIG. 1 is a perspective view of one embodiment of the apparatus of the invention.

With particular reference to FIG. 1, the details of the apparatus of the invention will now be described.

As stated, the method of the invention is for testing containers; for example, nail polish bottles, to determine those which might have checks in areas of the base of the finish of the container which are difficult to inspect by existing optical means. The present invention takes the form of apparatus which will impact the finish of the container at 4, spaced, circumferential points around the container finish to segregate or to eliminate those containers having defective necks.

The apparatus is mounted on a supporting rail, generally designated 10, which serves to support a horizontal conveyor 11. The conveyor 11 is moving in the direction of the arrows shown. A pair of guide rails 12 and 13, shown to the left of FIG. 1, will guide containers "C" into the operative test area of the invention. While the conveyor is schematically shown as a belt, in actual practice, it is a flex top, link type chain conveyor, which is supported along its length in the test area of the invention. As can be seen from FIG. 1, the rails 12 and 13 are in alignment with a side rail 14, which extends through the testing zone. The side rail 14 is supported from the rail 10 by bracket arms 15. The arms 15 are bolted to ears 16, connected to the back of the rail 14. With the particular arrangement of connecting the ears 16 to the bracket arms 15, the rail 14 may be tilted to accommodate bottles which are not of a right cylindrical shape. Opposed to the rail 14 is a side rail 17. The side rail 17 serves as a backup member for a belt 18. The belt 18 extends along the front of the rail 17 and around a drive pulley 19, a tension pulley 20, and continues along the back of the test area, and about an idler pulley 21. The relative spacing of the rails 14 and 17 is such that when a container "C" enters between the two rails with the interposed belt 18, bottles, or containers "C" will be moved along in the direction of the arrow shown on the conveyor 11, and will be rotated about their axes at a preselected rate such that a container will rotate through at least 90° of its circumference between each testing position.

Figure 8:
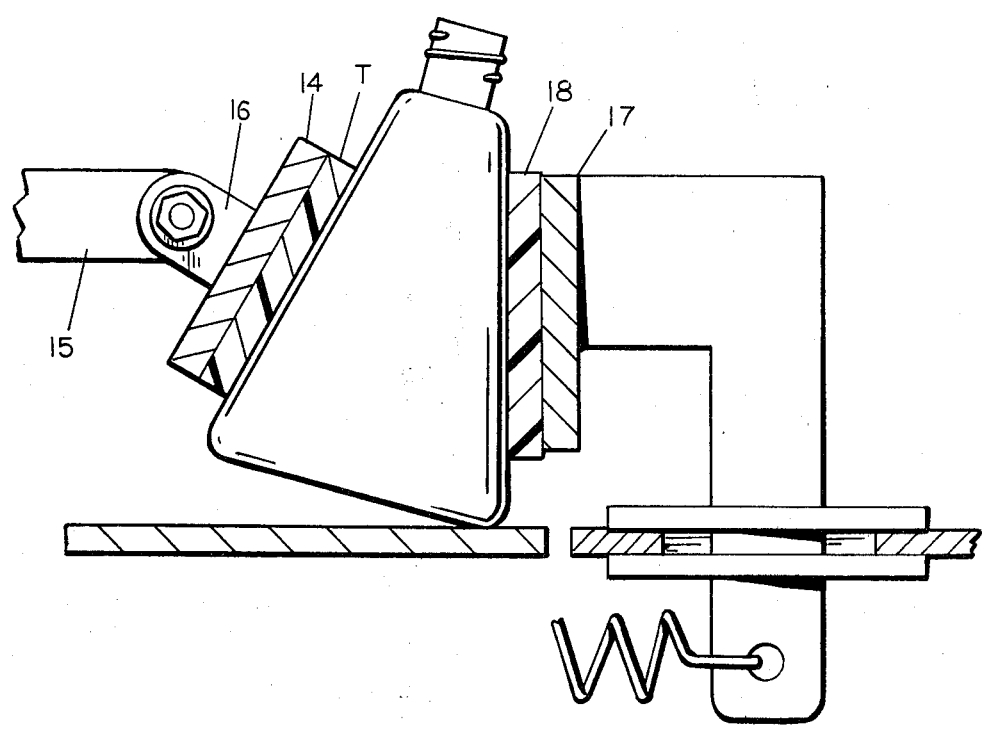
FIG. 8 is an end view of a modification on an enlarged scale of the system invention for handling ware that does not have vertical sidewalls relative to its base.

With particular reference to FIG. 8, it can be seen that a bottle of non-cylindrical, or one which does not have a vertical wall relative to the base, may be moved and rotated through the inspection zone while firmly held between the drive belt 18 and the rail 14. In this particular view, the rail 14 is shown faced with a wear resistent material T, such as teflon. The rails 14 and 17, as viewed in FIG. 1, guide bottles through the inspection or testing area and exit to the right, guided between two rails 22 and 23.

Figure 7:
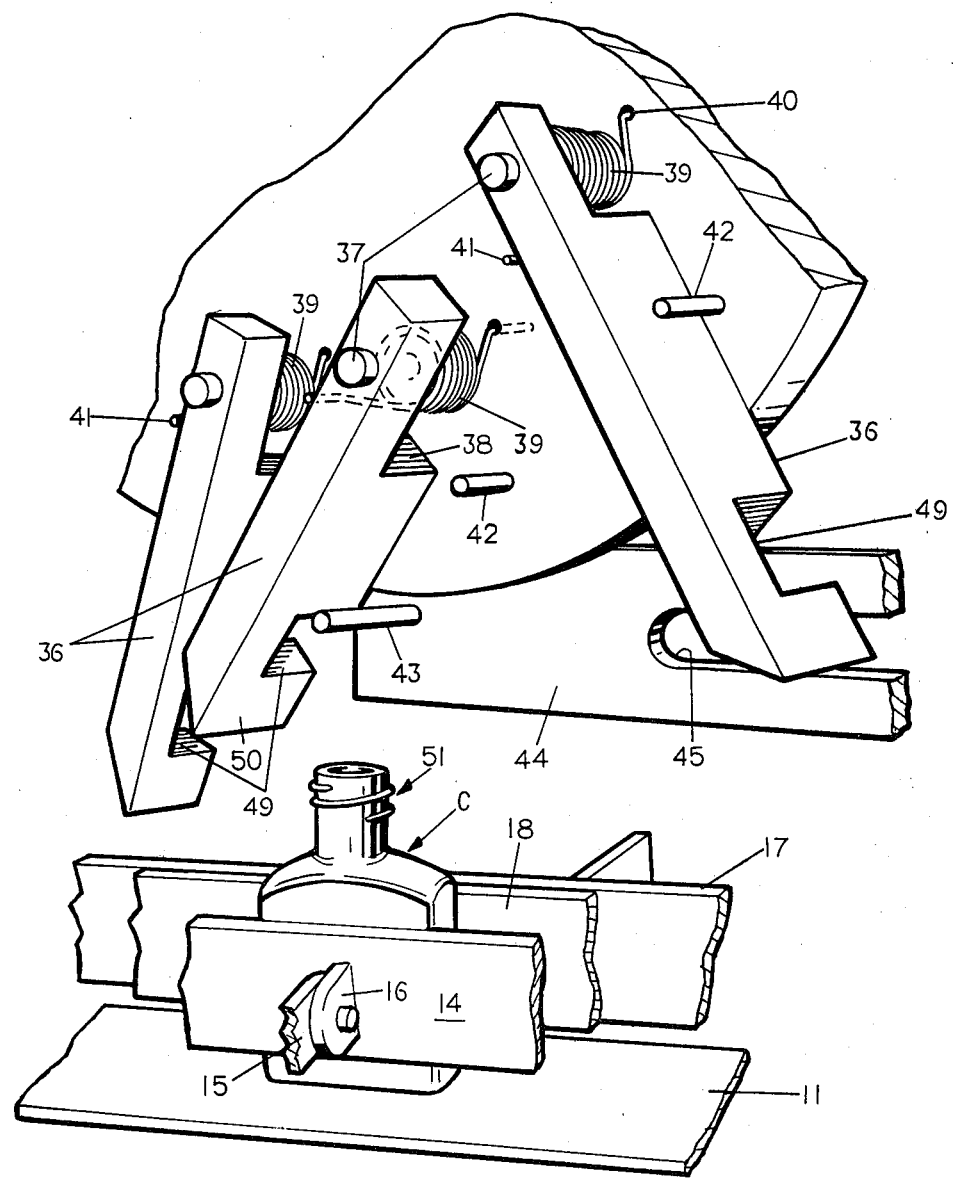
FIG. 7 is an enlarged perspective view of a portion of the apparatus of FIG. 6.

Mounted above the conveyor 11, and generally running parallel but not necessarily directly thereover, is a drive shaft 24 supported at one end in a bearing 25 and coupled to a shaft 26 at its opposite end by a coupling 27. The shaft 26 extends from a gear box 28 which is driven by a D.C. motor 29. D.C. motor 29 and the gear box 28 are mounted on a platform 30, which is supported above the conveyor 11 by a member 31. At spaced intervals along the shaft 24 are positioned four discs 32-35. Each disc is essentially identical and is provided with fourteen, radially extending, impact fingers 36. The following details are best seen with reference to FIG. 7, which is an enlarged partial view in perspective of one of the disc, and while not being a disc positioned relative to a container of the specific type shown in FIG. 1, it is a representative drawing of a finger used on all the discs in the present invention. Each finger 36 is mounted to the disc for pivotal movement about a pin 37. At the end of the finger 36 pivoted to the pin 37, the finger is provided with a cutout, or notch 38. The notch 38 provides room for a spiral spring 39. Spring 39 has one end thereof extending into a hole 40 provided in the disc 32, with the opposite end being bent outwardly, relative to the disc to which it is attached, with this bent end 41 bearing against the side of the individual finger about whose pivot pin 37 the spring is positioned. A stop pin 42, also fixed to the disc, will maintain the finger 36 in a particular position relative to the disc, with some spring tension applied by the spring 39 to hold the finger against the stop pin 42. At each position of the discs 32–35, there is provided a trip pin 43, as best seen in FIGS. 4 and 7. The trip pin 43 is carried at the extreme end of an adjustable supporting bar 44. As perhaps best shown in FIGS. 1 and 7, the bar 44 is provided with an elongated slot 45 formed therein. The slot serves as the means by which the bar 44 is bolted to a vertical plate 46. The plate 46 is in the form of an angle bracket which has a horizontal foot portion 47 with a bolt extending through the foot plate 47 and into an elongated slot 48 formed in the upper web of the rail 10. In this manner, the bar 44 may be positioned at selected places along the length of the rail 10, and thus provide adjustment to the position of the trip pin. This is a necessary accommodation to permit the adjustment of the discs 32–35 along the shaft 24. Thus it can be seen that there is a trip pin 43, and its supporting bar 44, corresponding to each of the discs 32–35 in the embodiment of FIG. 1. The embodiment of FIG. 1 is especially for inspecting or testing containers which may be rotated about their vertical axes as they move through the testing zone and are driven in rotation, individually, by the belt 18 engaging the side thereof. The trip pin functions as the disc rotates such that the trip pin 43, as viewed in FIGS. 4 and 7, engages the side of the finger 36 which is opposite to side which is engaged by the end 41 of the spring 39. As the disc continues to rotate in the direction of the arrow shown thereon, the pin will fall through a notch 49 provided in the finger, and at this point in time, the finger will have been preloaded by the spring 39 in the sense that it has been moved back away from the stop pin 42. When the trip pin 43 clears the notch 49, the finger 36 moves forward under the impetus of the spring 39 and its lower end portion 50 will engage the neck or finish portion 51 and impact the neck. In the event the finish is defective to the extent it will fail, the finger will, in effect, knock the neck or finish from the container. If the container is not defective, the finger will continue to ride over the finish of the container without harming the container in any way. The finger 36 that is used in the invention was made from a material such as Micarta, or nylatron which will not scratch the container surface.

Turning now to FIGS. 2–5, the operation of the finger is schematically shown in sequence and by reference to these figures it can be seen that as the disc 32 rotates, the stationary trip pin will be engaged by the finger 36, as illustrated in FIG. 3. One of the fingers 36 is shown as being rotated clockwise about its pivot relative to the disc 32 to the position illustrated in FIG. 4. Upon rotation of the disc 32 for a slightly greater degree than illustrated in FIG. 4, the trip pin 43 will fall through the notch 49, releasing the impact finger 36 so that it will swing into engagement with the finish of the container being tested as shown in FIG. 5. This is the functional sequence of the operation of a single finger impacting the finish of a container at one position.

The specific configuration illustrated in FIGS. 1–5, is that which pertains principally to the tester of the present invention when used to impact the finish of the containers that are rotatable about their axes. Rotation of each container between the position of each of the discs 32,33,34 and 35 will result in each container being impacted at 90° intervals from its position at the time of its impact by the previous disc. The testing unit will accept random flow of bottles without requiring any timing, indexing, or spacing device in advance of the tester, as has normally been the practice in the past. Since the tester accepts random flow of bottles, the best explanation is that at times there may not be any bottles in the drive belt section of the tester, and at other times there may be one, two, three or any number of bottles in the tester, or then again, it may be full with bottle to bottle contact. The disc rotation speed is set to correspond to the drive belt speed and each bottle will be contacted by a finger on each disc as the bottle randomly passes through the snap action finish tester of the invention. As the disc rotates, the spring loaded finger 36 on the disc contacts the stationary trip pin 43, as shown in FIG. 3. As the disc continues to rotate the sequence of the events illustrated in FIGS. 4 and 5 will occur. As the bottles travel in a single line on conveyor 11, they pass between the spring loaded drive belt 18 and the teflon coated backup rail 14. This serves two purposes: one, rotating the bottles to permit the finishes to be contacted each 90° of rotation by the fingers, and two, holding the bottle securely while the spring loaded fingers are physically impacting the finish of the bottle. As round bottles pass through the drive belt section, they rotate due to being squeezed between the stationary backup rail and the moving drive belt. The drive belt is controlled by a variable speed D.C. drive unit and may be run at whatever speed is necessary to handle production line speed. The discs 32–35, with the spring loaded fingers, are spaced perpendicular along the drive belt section so as to contact the bottle finish each 90° as the bottle rotates through the belt section.

It has been determined from experiments that bottle finishes need to be physically contacted each 90° to ensure all defective finishes are removed. This assures that a defect, such as a check, will never occur more than 45° from an impact. Spacing is determined by the bottle circumference. The first disc is positioned near the in-feed end of the drive belt section. The second, third and fourth discs numbered 33, 34 and 35 respectively, are located downstream at a distance which is a multiple of the bottle circumference in reference to the position of disc 32. Disc spacing equal to one-quarter bottle circumference would permit impact to finish at 90°; however, the width of the fingers and the discs is such that close spacing would be practically impossible to do because of interference from an adjacent disc. With this in view, the disc are normally spaced 1¼; 2¼ etc., times the bottle circumference from the first disc. This being such that each disc is 1¼ times the bottle circumference distance from the previous disc. After the spacing of the discs are set for a particular bottle diameter and the speed of the drive belt is set for the required production speed, then the speed of the disc with the spring loaded fingers, is set to correspond with the drive belt speed such that each bottle passing the disc will be contacted by a finger on a disc. The discs are controlled by a variable speed D.C. drive unit and can be run at whatever speed is necessary to handle production speeds without limit.

As a particular example, if a job is being run at 140 bottles per minutes, and the speed of the belt is set to pass 140 bottles per minute, then the disc with the spring loaded finger will have to be run at 10 revolutions per minutes since there are 14 fingers on each disc, to ensure that each bottle is contacted by at least one finger (10 RPMS × 14 fingers per RPM = 140 fingers per minute.) The disc can be run a little faster than 10, which means some finishes may be impacted more than one time at each 90° interval. Experience, however, indicates the discs should be run at a speed just fast enough to handle production requirement. This minimizes wear on the fingers and the equipment. The foregoing explanation covers the operation of the round ware tester.

Figure 6:
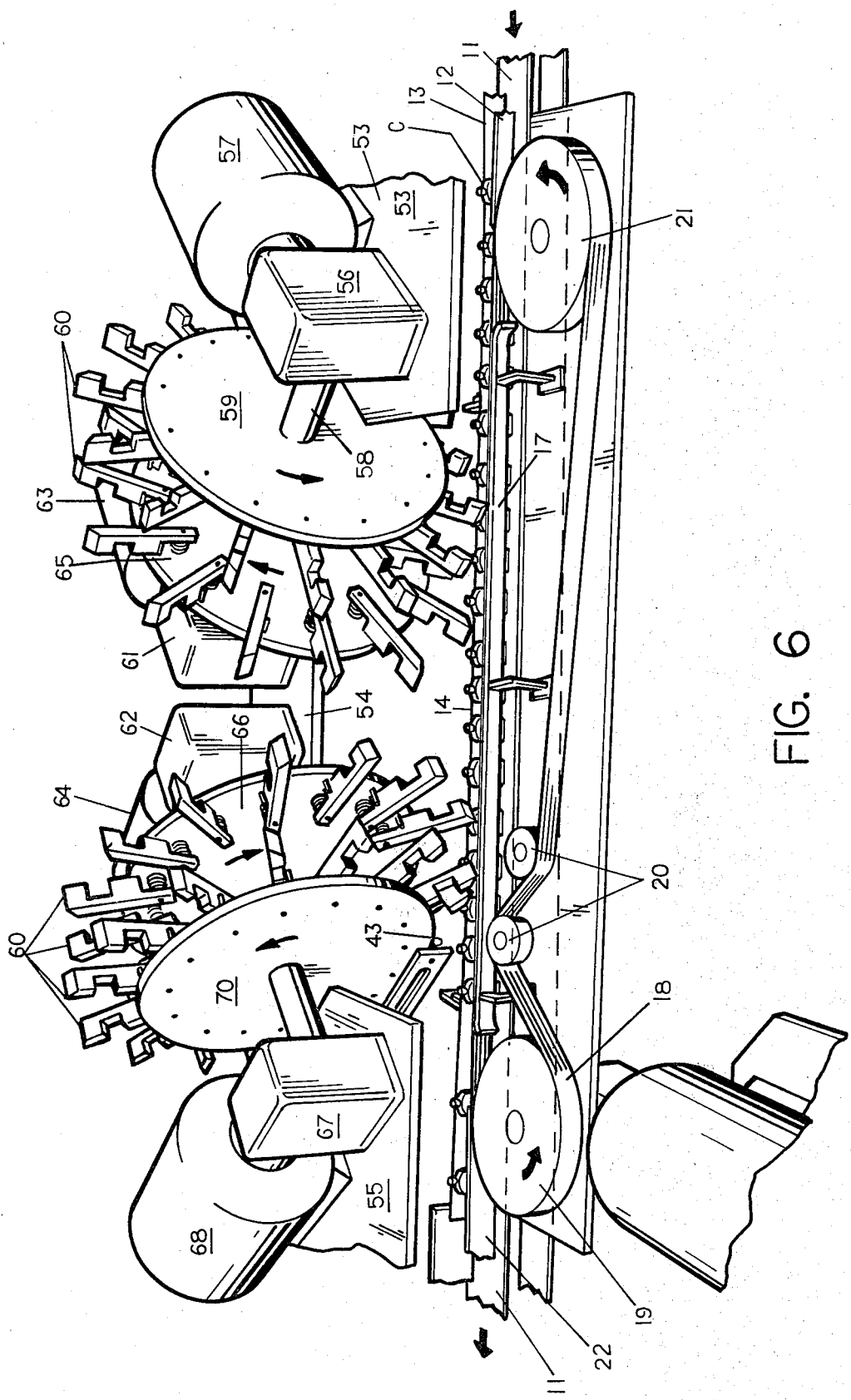
FIG. 6 is a perspective view of a second embodiment of the invention for testing non-round ware.

With particular reference to FIG. 6, a second embodiment of the invention will be described which is designed to handle non-round containers which are not capable of being rotated about their axes to position their finishes at 90° intervals relative to the discs carrying the impacting fingers. The non-round ware finish tester of FIG. 6 also will accept random flow bottles. The only difference between the embodiment shown in FIG. 1, and that shown in FIG. 6, is the manner in which the disc is mounted over the drive belt section of the testing machine. The operation and comments with regard to the spring loaded fingers and trip pins for the non-round tester is the same as that described previously in relation to FIG. 1. With reference to FIG. 6, it should be pointed out that the common elements found in FIG. 6 to those found in FIG. 1, have been given the same reference numerals.

In the embodiment shown in FIG. 6, the containers "C" are of a non-round configuration, and such a typical container is specifically shown in FIG. 7 on a somewhat larger scale. Positioned adjacent the side of the conveyor are 3 platforms 53, 54 and 55. The platform 53 supports a gear box 56 and a D.C. motor 57. The output shaft from the gear box 56 is connected to a disc 59. The disc 59 is provided with a plurality of pivotally mounted impact fingers 60. Fingers 60 are the same as fingers 36 previously described in respect to FIGS. 1 and 7. These fingers are mounted to the disc in the same manner indicated with respect to those in FIGS. 1 and 7 and are functionally operated by appropriately positioned trip pins which are given the reference numeral 43. The platform 54 is shown supporting two gear boxes 61 and 62. The gear box 61 is connected to a motor 63 and the gear box 62 is connected to a motor 64. The gear box 61 has an output shaft which is coupled to a disc 65 which is rotated in the direction of the arrow, as shown thereon. The gear box 62 has an output shaft coupled to a disc 66 which is rotated in the direction of the arrow, as shown thereon. It should be pointed out that the discs 65 and 66 have impact fingers 60 mounted thereon in the manner taught by the above description relative to FIGS. 1 and 7. The platform 55 supports a gear box 67 and a motor 68. The gear box 67 has an output shaft 69 coupled to a disc 70 and the disc 70 is rotated in the direction of the arrow shown thereon, and carries a plurality of impact fingers 60. It should be pointed out that the vertical planes in which the discs are positioned are at a 45° angle relative to the direction of movement of the ware, and the direction of rotation of adjacent disc are opposite thus providing an arrangement where each container finish will be impacted by an impact finger at 90° intervals around the circumference of the finish. As the non-round bottles travel on the single line conveyor 11, they randomly pass through between a spring loaded, "rough top" drive belt 18 and a teflon coated backup rail 14. The non-round bottles do not precess, they are pulled through the test section by the drive belt, due to being squeezed between the stationary backup rail and the moving drive belt. The squeezing action holds the bottle securely while the spring loaded impact fingers are physically impacting the finish of the containers. The drive belt, which is controlled by a variable speed D.C. drive unit, is run at whatever speed is necessary to handle production lines speed. Since the non-round ware cannot rotate through the drive belt inspection section, the discs with the spring loaded fingers are positioned at fixed 45° angles along the drive belt section, so as to contact the bottle finish each 90° as the bottle passes through the drive section. Each bottle finish therefore is contacted by a finger at clock directions of 1:30, 4:30, 7:30 and 10:30. This means that a defect, such as a check, would never be more than 45° from an impact. Unlike the round ware tester, as set forth in FIG. 1, the discs in this embodiment do not have to be re-positioned for different sizes or types of non-round ware to be assured of impacting the finish at each 90°. For example, as a non-round bottle passes by the disc 59 in the drive belt section, it is contacted by a spring loaded finger 60 on the disc 59 at 10:30. As the bottle continues to travel through the drive section and passes by the disc 65, it is contacted by a spring loaded finger on the disc 55 at 4:30. As the bottle continues to travel through the drive section and passes by the disc 66, it is contacted by a spring loaded finger on the disc 66 at 1:30. As the bottle continues to travel through the drive section, it will pass the disc 70 and will be contacted by a spring loaded finger at 7:30. After the speed of the drive belt is set for required production speed, then the speed of the discs with the spring loaded fingers are set. The speed of the discs are set to correspond with the drive belt speed so that each bottle passing the discs will be contacted by a finger on each disc. Thus it can be seen that the containers to be inspected are impacted at 90° intervals around the finish. In the set up of the invention the finger is set to extend about ¼ inch below the top of the finish to insure that the finish is given a meaningful impact. Other and further embodiments may be resorted to within the spirit and scope of the attached claims.

I claim:

1. Apparatus for testing glass containers to determine whether the finish thereof is weak or acceptable comprising a conveyor for moving a series of containers into a test zone, a pair of opposed guide rails overlying said conveyor for guiding containers, in series, through the test zone, a horizontally driven belt positioned between one of said guide rails and the side of the containers for moving the containers through the test zone, at least four spring loaded impact fingers spaced along said conveyor in said test zone, and means for releasing said fingers successively into contact with the finish of the containers at circumferentially spaced intervals therearound.

2. The apparatus of claim 1 wherein said horizontally driven belt in engagement with the side of the containers rotates the containers about their vertical axis through the test zone and said one of said guide rails is spring biased in opposing relationship to the other guide rail.

3. The apparatus of claim 1 wherein said spring loaded impact fingers are carried by rotatable discs, said fingers extending radially outward beyond the periphery of the disc, a stop pin carried by the disc in engagement with each of the fingers, and said means for releasing said fingers comprises a trip pin mounted in the path of the finger movement and engageable by the finger upon rotation of the disc.

4. The apparatus of claim 3 wherein each finger is formed with a notch through which the trip pin will pass upon rotation of the disc a predetermined amount.

5. The apparatus of claim 3 wherein said finger carrying discs are four in number.

6. The apparatus of claim 5 wherein all four discs are mounted on a common shaft, and motor means connected to said shaft for rotating said discs in the same direction.

7. The apparatus of claim 6 wherein said discs are mounted on said shaft for adjustment longitudinally and circumferentially thereof.

8. The apparatus of claim 5 wherein each disc is mounted for rotation about an axis which is at an approximate 45° angle to the direction of movement of the containers.

9. The apparatus of claim 8 wherein a first pair of said discs are mounted for rotation about parallel axes in opposite directions.

10. The apparatus of claim 9 wherein the other two discs are also mounted for rotation about parallel axes in opposite directions but with their axes at 90° with respect to the axes of the first pair of discs.

11. The apparatus of claim 10 further comprising motor means connected to each disc for rotating each disc individually.

* * * * *